US012629165B2

(12) United States Patent
Vleugels

(10) Patent No.: US 12,629,165 B2
(45) Date of Patent: May 19, 2026

(54) FORCEPS CONSTRUCTION, SURGICAL INSTRUMENT AND SURGICAL INSTRUMENT COMPRISING SUCH FORCEPS CONSTRUCTION

(71) Applicant: EFI Holding B.V., Maastricht (NL)

(72) Inventor: Michel Petronella Hubertus Vleugels, Maastricht (NL)

(73) Assignee: EFI Holding B.V., Maastricht (NL)

( * ) Notice: Subject to any disclaimer, the term of this patent is extended or adjusted under 35 U.S.C. 154(b) by 799 days.

(21) Appl. No.: 17/293,585

(22) PCT Filed: Nov. 15, 2019

(86) PCT No.: PCT/NL2019/050748
§ 371 (c)(1),
(2) Date: May 13, 2021

(87) PCT Pub. No.: WO2020/101496
PCT Pub. Date: May 22, 2020

(65) Prior Publication Data
US 2022/0008094 A1      Jan. 13, 2022

(30) Foreign Application Priority Data
Nov. 16, 2018    (NL) ..................................... 2022017

(51) Int. Cl.
*A61B 17/29*      (2006.01)
*A61B 90/00*      (2016.01)
*A61B 17/00*      (2006.01)

(52) U.S. Cl.
CPC .......... *A61B 17/2909* (2013.01); *A61B 90/06* (2016.02); *A61B 2017/00398* (2013.01); (Continued)

(58) Field of Classification Search
CPC ............ A61B 17/2909; A61B 17/2926; A61B 2017/2946; A61B 2090/064; A61B 2562/0266
See application file for complete search history.

(56) References Cited

U.S. PATENT DOCUMENTS 5,964,780 A * 10/1999 Balazs ....................... B25J 1/04
606/208
9,622,763 B2* 4/2017 van den Dool ........ A61B 17/29
(Continued)

FOREIGN PATENT DOCUMENTS

WO          01/84097 A1      11/2001
WO          03/020139 A2      3/2003

*Primary Examiner* — Elizabeth Houston
*Assistant Examiner* — Jonathan A Hollm
(74) *Attorney, Agent, or Firm* — Hoffmann & Baron, LLP

(57) ABSTRACT
A forceps construction includes a forceps frame having a distal end, the distal end including a first extension and a second extension, the first extension and the second extension extending in distal direction from a main part of the forceps frame, a first jaw element rotatably mounted on the first extension, a second jaw element rotatably mounted on the second extension, an actuation assembly connected to the first jaw element and the second jaw element to rotate the first jaw element and the second jaw element with respect to the forceps frame. A surgical instrument, for example a surgical instrument for minimally invasive surgery, includes a frame and a jaw element.

14 Claims, 5 Drawing Sheets

(52) U.S. Cl.
CPC ................. *A61B 2017/2926* (2013.01); *A61B 2017/2929* (2013.01); *A61B 2017/2946* (2013.01); *A61B 2090/064* (2016.02); *A61B 2562/0266* (2013.01)

(56) References Cited

U.S. PATENT DOCUMENTS

| | | |
|---|---|---|
| 2009/0076534 A1 | 3/2009 | Shelton, IV et al. |
| 2012/0138658 A1 | 6/2012 | Ullrich et al. |
| 2016/0030240 A1 | 2/2016 | Gonenc et al. |

\* cited by examiner

Fig. 9
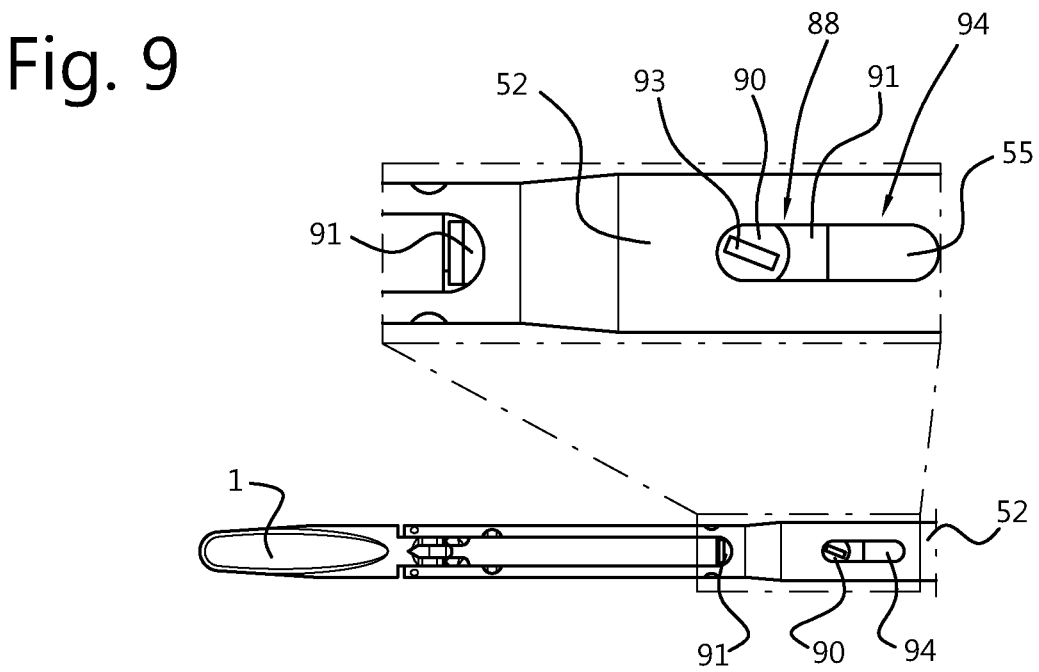
Fig. 10
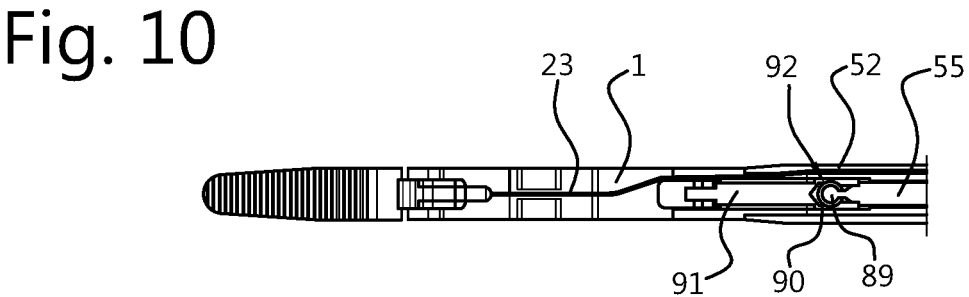
Fig. 11

FORCEPS CONSTRUCTION, SURGICAL INSTRUMENT AND SURGICAL INSTRUMENT COMPRISING SUCH FORCEPS CONSTRUCTION

CROSS-REFERENCE TO RELATED APPLICATIONS

This application is the National Stage of International Application No. PCT/NL2019/050748, filed Nov. 15, 2019, which claims the benefit of Netherlands Application No. 2022017, filed Nov. 16, 2018, the contents of which is incorporated by reference herein.

FIELD OF THE INVENTION

The present invention relates to a forceps construction, for example a forceps construction for use in a surgical instrument for minimally invasive surgery. Such surgical instrument, usually, comprises an elongated frame having a small cross-section that is introduced via an incision into a body of a patient. To manipulate tissue, for example hold, pull or palpate tissue, the surgical instrument comprises a forceps construction comprising a first jaw element and a second jaw element that are rotatably mounted on a forceps frame. The surgical instrument comprises a trigger device, for example a handle or any other suitable actuator or mechanism for operating the first jaw element and the second jaw element of the forceps construction.

BACKGROUND OF THE INVENTION

It is of importance to apply an appropriate force to the first and the second jaw element such that tissue is manipulated with a suitable manipulation force. This force should not be too low to prevent that tissue is inadvertently released from the forceps, but also not too high to avoid damage of the tissue. Therefore, it is also of importance to provide accurate feedback of the applied force to the trigger device such that a surgeon can feel the actually applied force, or a force representative for this applied force.

An embodiment of an instrument for minimally invasive surgery is known from WO 03/020139. In the known embodiment of a surgical instrument the force exerted on the forceps by a surgeon is measured by a force sensor arranged on a jaw of the forceps and is fed back to the surgeon via a control unit. In this way the surgeon is provided with a better feeling of the applied force. The force sensor may for example be an optical sensor connected by means of an optical fibre to a suitable control unit.

U.S. Pat. No. 9,622,763 discloses a surgical instrument comprising a forceps construction in which force sensors are arranged on the forceps frame, instead of on the jaw elements, to determine the force applied on the first and second jaw elements.

The forceps construction of U.S. Pat. No. 9,622,763 comprises:

a forceps frame having a distal end, the distal end comprising a first extension and a second extension, the first extension and the second extension of extending in distal direction from a main part of the forceps frame. The first extension and the second extension extend in parallel in the distal direction with a slot, slit or gap between the first extension and the second extension.

A first jaw element is rotatably mounted on the first extension and a second jaw element is rotatably mounted on the second extension. An actuation assembly connected to the first jaw element and the second jaw element is provided to rotate the first jaw element and the second jaw element with respect to the forceps frame.

The presence of the slit, slot or gap results in bending of the first extension and the second extension when a force is exerted on the first jaw element and/or the second jaw element. Thus, by measuring this bending of the first extension and/or the second extension, the force exerted on the first jaw element and/or second jaw element may be measured.

For this reason, a strain sensor is mounted at or near the end of the slit between the first extension and the second extension. However, at this location also other forces are present in the forceps frame, such as pulling or pushing forces in the forceps frame resulting from operating the first and second jaw elements. These other forces will also be measured by the strain sensor, and the force exerted on the first and/or second jaw element cannot reliably be determined on the basis of the force determined by the strain sensor at this location. Therefore, U.S. Pat. No. 9,622,763 proposes to mount a second strain sensor on the forceps frame on a location spaced from the slit between the first extension and the second extension. This location is selected such that the strain resulting from bending of the first extension and the second extension is not measured by the second strain sensor, but the other forces in the forceps frame are measured by the second strain sensor. A further strain sensor may be provided to determine temperature effects on the measurements.

By comparison of the measurement results of the first strain sensor and the second strain sensor, the strain resulting from bending of the first extension and/or the second extension may be determined. On the basis thereof, the force exerted on the first jaw element and/or the second jaw element may be calculated.

It is a drawback of the surgical instrument of U.S. Pat. No. 9,622,763 that multiple, at least three strain sensors are required to determine the force that is exerted on the first jaw element and/or the second jaw element of the forceps construction. This results in a relatively complex measuring system and requires an additional calculation effort, i.e. processing time, to determine the force that is exerted on the first jaw element and/or second jaw element.

SUMMARY OF THE INVENTION

It is an object of the invention to provide a forceps construction, in particular a forceps construction for a surgical instrument to be used in minimally invasive surgery, wherein the force exerted on the first and/or second jaw element can be determined with a high degree of accuracy, or at least to provide an alternative forceps construction.

The invention provides a forceps construction comprising a forceps frame having a distal end, the distal end comprising a first extension and a second extension, the first extension and the second extension extending in distal direction from a main part of the forceps frame, a first jaw element rotatably mounted on the first extension, a second jaw element rotatably mounted on the second extension, an actuation assembly connected to the first jaw element and the second jaw element to rotate the first jaw element and the second jaw element with respect to the forceps frame, characterized in that the first extension comprises a first distal extension part, a first proximal extension part and a first bridge element connecting the first distal extension part and the first proximal extension part, wherein the first bridge element is designed to facilitate bending of the first distal extension part with respect to the first proximal extension part when a force is exerted on the first jaw element, the second distal extension comprises a second distal extension part, a second proximal extension part and a second bridge element between the second distal extension part and the second proximal extension part, wherein the second bridge element is designed to facilitate bending of the second distal extension part with respect to second proximal extension part when a force is exerted on the second jaw element, and in that a strain element is provided between the first extension and the second extension, wherein a proximal end of the strain element is connected to the main part of the forceps frame, and wherein a distal end of the strain element is connected to a proximal end of the first distal extension part and a proximal end of the second distal extension part, such that a force exerted on the first jaw element and/or the second jaw element results in bending of the first extension at the first bridge element and/or the second extension at the second bridge element, respectively, and consequently in elongation or compression of the strain element.

In the forceps construction of the invention a strain element is provided between the first extension and the second extension. This strain element is fixed at its proximal end to the forceps frame and at its distal end to the proximal ends of the first distal extension part and the second distal extension part. This strain element is provided as a basis to mount a strain sensor.

Bending of the first extension and/or second extension due to forces being exerted on the first jaw element and/or second jaw element will result in elongation of the strain element. This elongation may be measured by the strain sensor mounted on or in the strain element.

Other forces exerted on the forceps frame, such as pulling or pushing forces resulting from actuating movement of the first and second jaw element will be transmitted through the first extension and the second extension, but these forces will substantially not be transmitted through the strain element. As a result, there is no need for an additional sensor to measure these forces separately and subsequently correct the measurement of the first strain sensor for these other forces. In other words, the strain element is mechanically substantially isolated from other forces, such as pulling or pushing forces, in the forceps frame, and will therefore substantially only measure the strain resulting from bending of the first extension and/or second extension. On the basis of this measured strain, the forces exerted on the first jaw element and/or the second jaw element may relatively easily be calculated.

The first extension comprises a first bridge element between the first distal extension part and the first proximal extension part, wherein the first bridge element is designed to facilitate bending of the first extension when a force is exerted on the first jaw element, and the second extension comprises a second bridge element between the second distal extension part and the second proximal extension part, wherein the second bridge element is designed to facilitate bending of the second extension when a force is exerted on the second jaw element.

To improve the measurement results it is advantageous that the first extension and the second extension relatively easily deform, e.g. bend, at a desired location. To facilitate bending of the first extension a first bridge element is arranged between the first distal extension part and the first proximal extension part. This first bridge element is designed such that the first extension will mainly bend at the first bridge element when a force is exerted on the first jaw element. The bridge element may for example have a smaller cross section than the cross section of the first distal extension part and the first proximal extension part to facilitate bending of the first extension at the first bridge element. Correspondingly, a second bridge element is arranged between the second distal extension part and the second proximal extension part to facilitate bending of the second extension.

In an embodiment, the strain element is an elongated element. An elongated strain element provides a suitable shape for mounting a strain sensor to measure strain of the strain element.

In an embodiment, a cross section of the strain element is small compared with the cross section of the first bridge element and the second bridge element. By giving the strain element a relatively small cross section, it may further be prevented, or at least minimized, that pulling or pushing forces in the forceps frame will be transmitted through the strain element.

In an embodiment, the strain sensor is a Fibre Bragg Grating (hereinafter also FBG), or multiple FBG's, arranged in an optical fibre that is fixed on or in the strain element. It is found to be advantageous to use FBG sensors. An example of the FBG sensor is described in WO01/84097 A1 and will not be explained here in detail. An application of the FBG sensors as strain sensor is advantageous because a wavelength shift is proportional to a degree of strain, which is independent of any loss in the signal intensity thereby improving accuracy of force measurement. Furthermore, a FBG does not use any electrical signals near the sensitive measurement area. This is especially important in minimally invasive surgery instruments, which tend to include high voltage and high frequency electrical signals for surgical purposes, such as cutting.

In an embodiment, the optical fibre with the FBG is fixed in a hollow space in the strain element. In an alternative embodiment the optical fibre with the FBG may be fixed at any other suitable position on or in the strain element.

In an embodiment, the main part comprises in proximal direction from the strain element a hollow channel in which the optical fibre is arranged. From the strain element, the optical fibre comprising the Fibre Bragg Grating runs towards the proximal end of the forceps construction. By providing a hollow channel in the main part of the forceps frame, the optical fibre may run through the frame where it is protected from external influences.

In an embodiment, the optical fibre comprises a second Fibre Bragg Grating (FBG) arranged in the hollow channel to determine temperature effects. FBG sensors are sensitive for temperature differences. By providing a second FBG at a location relatively close to the first FBG, but where it will not measure any forces exerted on the forceps frame, it will only measure strain differences due to temperature effects. These measured strain differences can be used to compensate the measurements of the FBG fixed to the strain element for temperature effects.

In an embodiment, bending of the first extension with respect to the second extension is mechanically limited. Although elastic deformation due to bending of the first extension and the second extension is used to determine the forces exerted on the first jaw element and/or the second jaw element, it is desirable that the bending of the first extension and the second extension remains below certain maximum bending limits. In particular, it is undesirable that plastic deformation occurs in the first and/or second extension as a result of the bending of the first extension and second extension. To prevent that deformation beyond the maximum yield limits may occur, the bending range of the first extension and the second extension is limited by mechanical limiters, for example stop elements.

In such embodiment, the first extension may comprise a first bulge and the second extension may comprise a second bulge, wherein the first bulge and the second bulge have interlocking shapes to mechanically limit the bending of the first extension with respect to the second extension.

The forceps construction according to the invention may be applied in any suitable device or instrument, in which accurate force feedback of the force exerted on the first jaw element and/or the second jaw element is required. The forceps construction is in particular suitable to be applied in a surgical instrument, for example for minimally invasive surgery.

The invention therefore further provides a surgical instrument, for example for minimally invasive surgery, comprising:

an elongate frame comprising at its distal end the forceps construction of any of the preceding embodiments, a trigger device to operate the first jaw element and the second jaw element, an actuation rod provided between the trigger device and the actuation assembly to transfer an actuation force from the trigger device to the first jaw element and the second jaw element, a strain sensor mounted on or in the strain element to provide a sensor signal, and an actuator to exert a feedback force on the trigger device on the basis of the sensor signal.

In an embodiment, the strain sensor is a Fibre Bragg Grating provided in an optical fibre.

In an embodiment, the surgical instrument comprises an interrogator device to interrogate the Fibre Bragg Grating. The interrogator device may be integrated in a handheld surgical instrument, but may also be arranged in a separate housing that can be arranged in a stationary location, whereby other parts of the surgical instrument such as the elongate frame, trigger device, actuation rod, actuator and the forceps construction are provided as a handheld device. In another embodiment, the surgical instrument may also be integrated in a surgical robot.

In an embodiment, the surgical instrument comprises a controller wherein the controller is arranged to control the actuator on the basis of the sensor signal. The controller may be part of a handheld surgical instrument or device, but may in another embodiment be provided at another location, for example in a separate housing and/or integrated with the interrogator device.

Another aspect of the invention relates to a surgical instrument, for example a surgical instrument for minimally invasive surgery, comprising:

an elongate frame, at least one jaw element mounted movably at a distal end of the elongate frame, a trigger device to operate the at least one jaw element and arranged at a proximal end of the elongate frame, an actuation rod provided between the trigger device and the at least one jaw element, a sensor, for example a strain sensor, to provide a sensor signal representative for a force exerted on the at least one jaw element, and an actuator to exert a feedback force on the trigger device on the basis of the sensor signal, wherein the elongate frame comprises a handle part and a shaft, wherein the trigger device and the actuator are mounted on the handle part and the at least one jaw element is mounted on the shaft.

In an embodiment, the shaft has a longitudinal axis, wherein the shaft is rotatably, about its longitudinal axis, mounted on the handle part, wherein the sensor comprises an optical fibre, wherein the surgical instrument comprises a fibre guide to guide the optical fibre in a substantially helix shaped path concentric with the longitudinal axis.

To allow different rotational positions of the at least one jaw element with respect to the handle part of the surgical instrument, the shaft may be rotatably mounted, about its longitudinal axis on the handle part of the surgical instrument. A rotatable connection device may be provided between the handle part and the shaft to allow this rotation of the shaft with respect to the handle part. By rotation of the shaft, the position of the at least one jaw element with respect to the shaft may be adapted. This rotation of the shaft can for example be a manual rotation. A rotation knob rotatably fixed on the shaft, may be provided to carry out the manual rotation of the shaft.

The rotation of the shaft about its longitudinal axis may for example be in the range of 300 degrees to 360 degrees, for example in the range of 160 degrees to 170 degrees in both rotation directions from a middle rotation position of the shaft.

When the sensor comprises an optical fibre, for example in case of a Fibre Bragg Grating, the optical fibre may run through both the handle part and the shaft. Such optical fibre has to be able to follow rotation of the shaft with respect to the handle part, i.e. rotation of the shaft with respect to the handle part should not result in damage and/or performance loss of the optical fibre. When the optical fibre is arranged on the axis of rotation of the shaft, the optical fibre should be able to torque or twist about its longitudinal axis to follow the rotation of the shaft. An optical fibre will easily damage when the optical fibre is subject to such torque. Moreover, it is desirable to arrange the actuation rod on the axis of rotation.

When the optical fibre is arranged at a distance from the axis of rotation, rotation of the shaft will lead to a difference in length of the path of the optical fibre in the handle part and/or the shaft. The optical fibre should be arranged in surgical instrument such that the surgical instrument allows this change in path length of the optical fibre.

Furthermore, it should be avoided that the bending radius of the optical fibre becomes too small as a bend below a minimum fibre bending radius may have a negative effect on the optical performance of the optical fibre. For example, the bending radius of an embodiment of a typical optical fibre, for example having a diameter of 0.008 mm, suitable for use in a surgical instrument according to an aspect of the invention, should not be lower than 12 mm.

To facilitate rotation of the shaft without increased risk on damage of the optical fibre, the surgical instrument may comprise a fibre guide to guide the optical fibre in a substantially helix shaped path concentric with the longitudinal axis of the shaft. This fibre guide ensures that the change in path length can be accommodated by allowing the diameter of the loops of the optical fibre in the helix shape to increase or decrease in dependence of the rotation of the shaft with respect to the handle part. At the same time, the fibre guide ensures that the bending radius of the optical fibre will not come below a minimal bending radius. This minimal bending radius should be selected such that the optical fibre will have sufficient optical performance for the sensor measurement with the optical fibre.

The fibre guide may be formed as an element with an outer cylindrical surface, wherein the outer cylindrical surface comprises a helical groove to guide the optical fibre. The helical groove comprises a bottom surface defining the minimum bending radius of the optical fibre guided in the helical groove.

The helical groove comprises a number of helical revolutions of 360 degrees around the longitudinal axis of the helical groove. The number of revolutions is for example at least 3, preferably at least 5 revolutions. The number of revolutions is for example between 6 and 8 revolutions.

In an embodiment, the shaft is releasably mounted on the handle part, wherein the handle part supports a rotatable connection part arranged to mount the shaft on the handle part, wherein the optical fibre comprises a first fibre part arranged in the shaft and a second fibre part arranged in the handle part, wherein the surgical instrument comprises a fibre connection device to optically connect the first fibre part and the second fibre part, wherein the fibre connection device comprises a first connector arranged at the proximal end of the shaft and a second connector arranged at the distal end of the rotatable connection part.

It may be desirable to provide a shaft that is releasable from the handle part, for example to clean the shaft and the handle part separately. When an optical fibre is used as part of a sensor arranged in the shaft, a fibre connection device has to be provided to connect a first fibre part of the optical fibre arranged in the shaft with a second fibre part of the optical fibre arranged in the handle part.

Further, the shaft may be rotatable about its longitudinal axis. To enable a connection between the first fibre part and the second fibre part, a rotatable connection part may be supported by the handle part. The rotatable connection part may be fixed to the shaft to enable rotation of the shaft and to provide at the same time a connection between the first fibre part and the second fibre part. The fibre connection device may comprise a first connector arranged at the proximal end of the shaft and a second connector arranged at the distal end of the rotatable connection part.

To improve the connection between the first connector and the second connector the second connector may be biased by a spring element into the distal direction of the surgical instrument and/or the first connector may be biased by a spring element into the proximal direction of the surgical instrument.

In an embodiment, the trigger device comprises a trigger arranged to be manipulated by a user, wherein the trigger is rotatably mounted on the handle part of the frame, wherein the actuator is a linear direct drive motor comprising a coil and at least one permanent magnet assembly, wherein the coil is mounted on the trigger, and wherein the at least one permanent magnet assembly is mounted on the handle part.

In this embodiment the actuator is provided as a linear direct drive motor comprising a coil mounted on the trigger of the trigger device and at least one permanent magnet assembly mounted on the handle part. The actuation force of this linear direct drive motor is created directly between the trigger and the handle part of the frame of the surgical instrument. No separate moving parts are required and the coil and at least one permanent magnet assembly are spaced with respect to each other. As a result, the linear direct drive motor can relatively easily be cleaned when needed.

In an embodiment, the coil will move along a path of movement upon rotation of the trigger, wherein the actuator comprises two permanent magnet assemblies, each aligned with the path of movement at opposite sides of the path of movement.

In an embodiment, the at least one permanent magnet assembly comprises one or more permanent magnets and a back iron at a side of the magnets opposite to the side of magnets facing the coil.

In an embodiment, the at least one permanent magnet assembly comprises multiple permanent magnets arranged in a Halbach array. The advantage of the use of a Halbach array of permanent magnets is that the magnetic field of the permanent magnets is augmented at one side of the permanent magnets, i.e. the side of the permanent magnets facing the coil, while the magnet field at the opposite side of the permanent magnets can be cancelled to close to zero.

In an embodiment, the direct drive motor is a linear Lorentz motor. A Lorentz motor is a suitable motor to be used as actuator in the surgical instrument, as the motor can provide an actuation force without any direct mechanical contact between the coil mounted on the trigger and the at least one permanent magnet assembly mounted on the handle part of the frame of the surgical instrument.

In an embodiment, the shaft is a hollow tube, wherein the shaft and the actuation rod are, at their proximal ends, releasably mounted on the handle part, wherein the surgical instrument comprises an actuation rod locking mechanism to connect the actuation rod, at its distal end, to an actuation assembly of the at least one jaw element, wherein, in the assembled state, the actuation rod extends through the hollow shaft.

It may be advantageous to use a hollow shaft through which the actuation rod extends. To properly clean the actuation rod and the hollow shaft, it is desirable that the actuation rod can be taken out of the hollow shaft. In such embodiment an actuation rod locking mechanism to connect the distal end of the actuation rod with a proximal end of a lock element of the actuation assembly of the at least one jaw element may be required to release the actuation rod from the lock element in order to take the actuation rod out of the hollow shaft.

In an embodiment, the actuation rod locking mechanism comprises a spherical element mounted at the distal end of the actuation rod, and a catch element and a lock element mounted at the proximal end of the actuation assembly, wherein the lock element comprises a recess in which the catch element is placed, wherein the catch element comprises a catch space to receive the spherical element, wherein the catch element is rotatable between a locking position, in which the spherical element can be locked in the catch space of the catch element, and a non-locking position, in which the spherical element can move into and out of the catch space of the catch element.

It has been found that a catch element provided in a recess of the lock element can advantageously be used to lock the spherical element arranged at the distal end of the actuation rod.

In an embodiment, the actuation rod comprises a distal end surface and the lock element comprises a proximal end surface, wherein the catch element is arranged to pull, when the catch element is rotated from the non-locking position to the locking position the distal end surface against the proximal end surface. By exerting a pulling force on the actuation rod, while the proximal end surface of the lock element is pushed against the distal end surface of the actuation rod a tight connection between the lock element and the actuation rod can be obtained.

In an embodiment, the catch element comprises a driving surface, such as a slot, a groove, or a recess, to receive a tool head for rotation of the catch element between the locking position and the unlocking position, and wherein the shaft comprises an opening through which the tool head can be arranged on or in the driving surface. The rotation of the catch element between the locking position and the non-locking position can be performed by placing a tool head in the driving surface of the catch element. The driving surface is for example a groove in which a head of a screw driver can be arranged to transfer a rotating movement of the screw driver to the catch element.

Since the catch element is arranged in the hollow shaft an opening may be provided in the shaft through which a tool head of a tool, for example a screw driver, can be arranged in the groove of the catch element.

In an embodiment, the surgical instrument may comprise the forceps construction as described herein. In such embodiment the at least one jaw element mounted movably at a distal end of the elongate frame is part of the forceps construction.

BRIEF DESCRIPTION OF THE DRAWINGS

Embodiments of the aspects of the invention will now be described, by way of example only, with reference to the accompanying schematic drawings in which corresponding reference numerals indicate corresponding parts, and in which:

FIGS. 9, 10 and 11 show an actuation rod locking mechanism according to an embodiment of the invention.

DETAILED DESCRIPTION OF THE INVENTION

Figure 1:
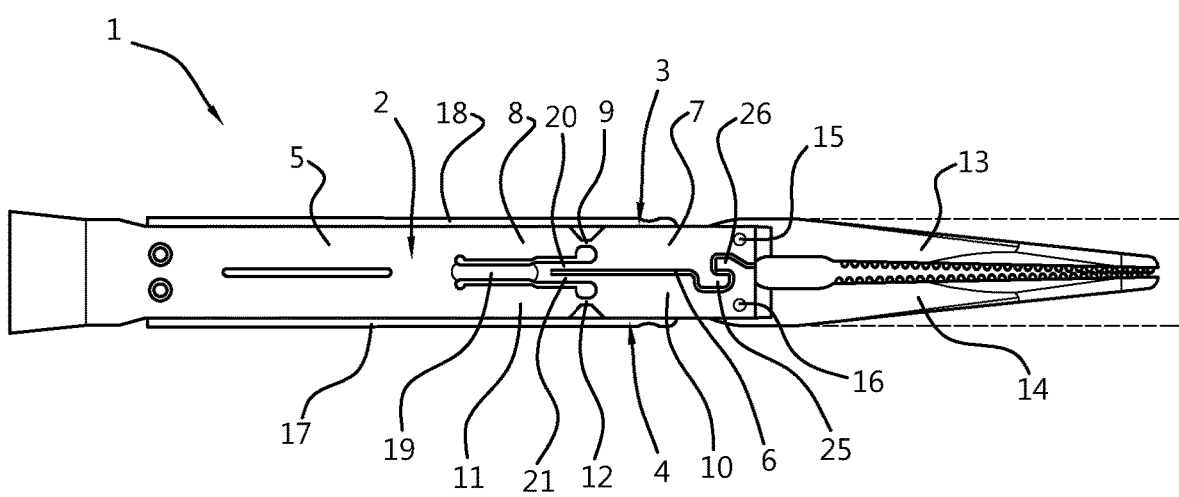
FIG. 1 shows a side view of a forceps construction according to an embodiment of an aspect of the invention with the jaw elements in closed position.
Figure 2:
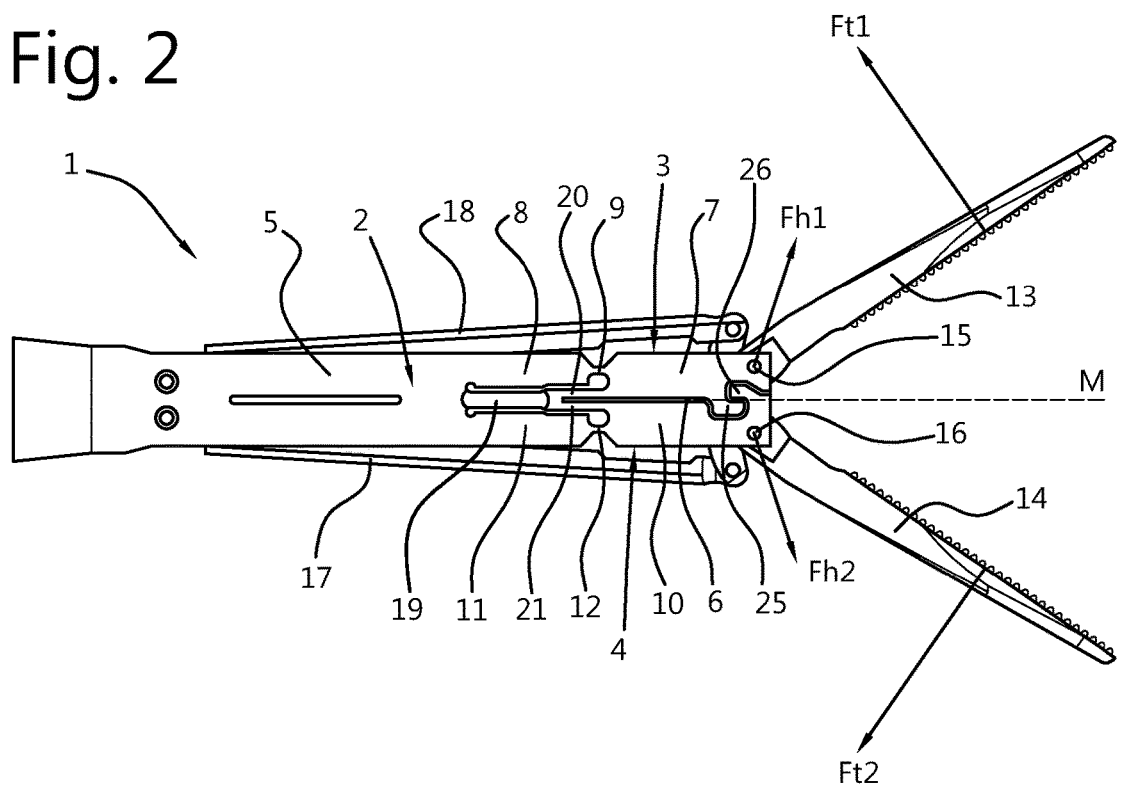
FIG. 2 shows a side view of a forceps construction of FIG. 1 with the jaw elements in open position.
Figure 3:
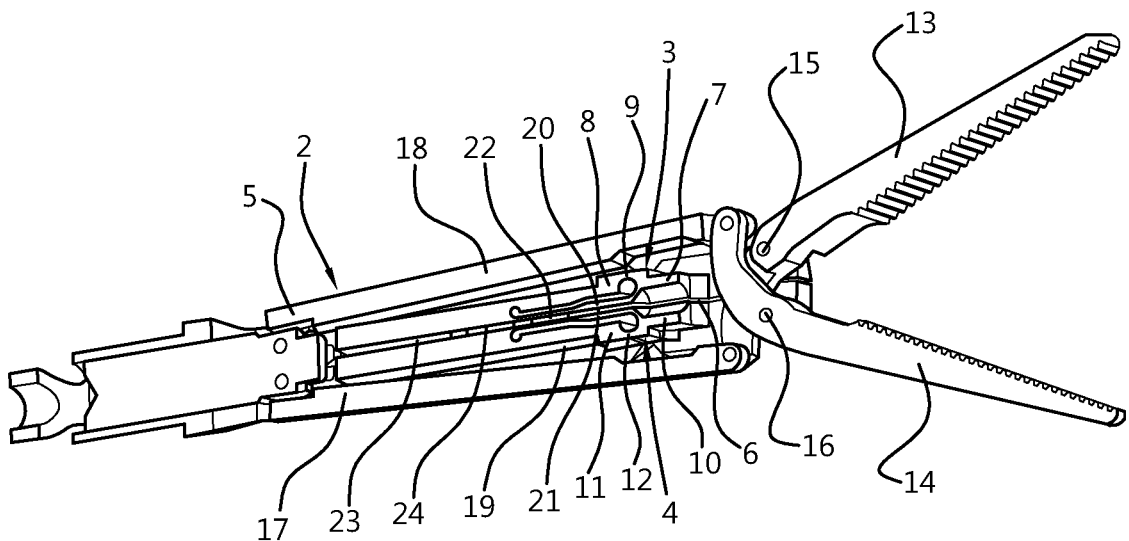
FIG. 3 shows a cross section of the forceps construction of FIG. 1.

FIGS. 1 and 2 show side views of a forceps construction generally denoted by reference numeral 1. FIG. 3 shows a cross section of the forceps construction 1.

The forceps construction 1 comprises a forceps frame 2. At the distal end of the forceps frame 2 a first extension 3 and a second extension 4 are provided. The first extension 3 and the second extension 4 extend in distal direction from a main part 5 of the forceps frame 2. A slit 6 is provided between the first extension 3 and the second extension 4. The first extension 3 and the second extension 4 in this embodiment are arranged parallel to each other. In other embodiments, the first extension 3 and the second extension 4 may be arranged at a non-zero angle with respect to each other.

The first extension 3 comprises a first distal extension part 7 and a first proximal extension part 8. The first distal extension part 7 and the first proximal extension part 8 are connected to each other by a first bridge element 9. The cross-section of the bridge element 9 is smaller than the cross sections of each of the first distal extension part 7 and the first proximal extension part 8.

Correspondingly, the second extension 4 comprises a second distal extension part 10 and a second proximal extension part 11, that are connected to each other by a second bridge element 12. The cross-section of the second bridge element 12 is also smaller than the cross sections of each of the second distal extension part 10 and the second proximal extension part 11.

The forceps construction 1 further comprises a first jaw element 13 and a second jaw element 14. The first jaw element 13 is rotatably mounted on the first distal extension part 7 at a first axis of rotation 15. The second jaw element 14 is rotatably mounted on the second distal extension part 10 at a second axis of rotation 16.

Figure 4:
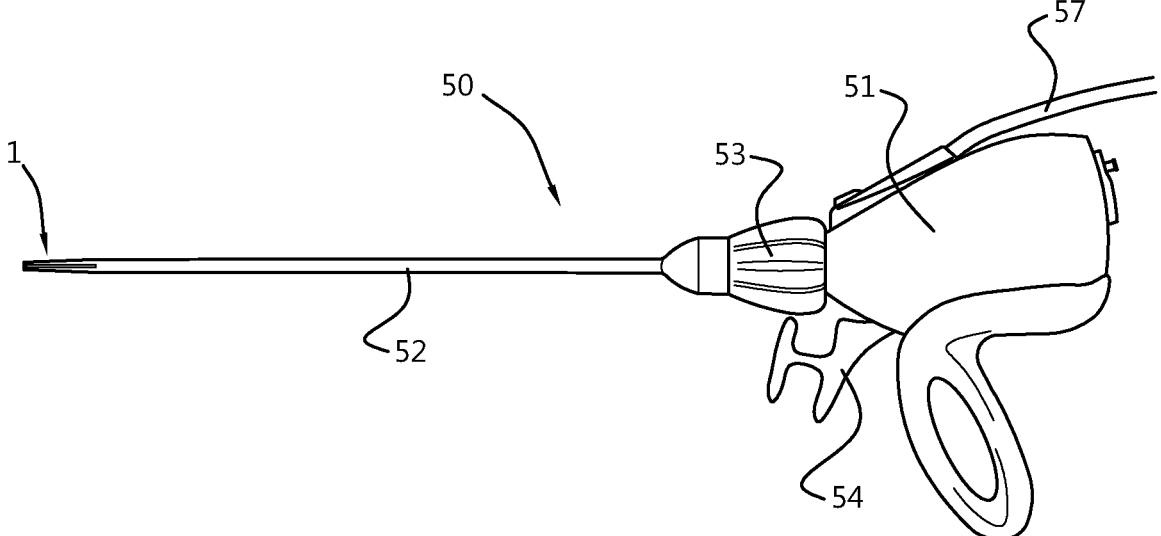
FIG. 4 shows a surgical instrument comprising the forceps construction of FIG. 1.

An actuation assembly is provided to rotate the first jaw element 13 and the second jaw element 14 with respect to the first axis of rotation 15 and the second axis of rotation 16. The actuation assembly comprises a first actuation element 17 connected to the first jaw element 13 and a second actuation element 18 connected to the second jaw element 14. The first actuation element 17 and the second actuation element 18 are connected or configured to be connected to an actuation rod that, in its turn, is connected to a trigger device for operating the forceps construction 1 (as shown in FIG. 4).

Between the first extension 3 and the second extension 4 a strain element 19 is provided. At its proximal end, the strain element 19 is connected to the main part 5 of the forceps frame 2, while the distal end of the strain element 19 is connected via a first connection part 20 to the proximal end of the first distal extension part 7 and via a second connection part 21 to the proximal end of the second distal extension part 10.

It is remarked that the first extension 3 and the second extension 4 are arranged at opposite sides of a midplane M. The first bridge element 9 and the second bridge element 12 are spaced from the midplane M, while the strain element 19 is arranged on the midplane M.

When a force Ft1 is exerted on the first jaw element 13, for example by tissue held between the first jaw element 13 and the second jaw element 14, this will result in a force Fh1 being exerted on the first axis of rotation 15. Similarly, when a force Ft2 is exerted on the second jaw element 14, for example by tissue held between the first jaw element 13 and the second jaw element 14, this will result in a force Fh2 being exerted on the second axis of rotation 16.

These forces Fh1 and Fh2 cause elastic deformation due to bending of the first extension 3 and the second extension 4. The first bridge element 9 and the second bridge element 12 are provided to facilitate this bending. Due to the force Fh1 the first distal extension part 7 tilts at the first bridge element 9 with respect to the first proximal extension part 8. Correspondingly, due to the force Fh2 the second distal extension part 10 tilts at the second bridge element 12 with respect to the second proximal extension part 11. Due to the tilting movement of the first distal extension part 7 about the first bridge element 9 and the tilting movement of the second distal extension part 10 about the second bridge element 12, the first connection part 20 and the second connection part 21 are pulled in the distal direction causing an elongation of the strain element 19.

The forceps construction 1 is designed such that the strain element 19 will only or substantially only be elongated by forces acting on the first axis of rotation 15 and the second axis of rotation 16 due to forces being exerted on the first jaw element 13 and the second jaw element 14, respectively. Other forces, in particular pushing and pulling forces caused by actuation of the first jaw element 13 and the second jaw element 14, will not or substantially not be transmitted through the strain element 19, but will be transmitted through the first bridge element 9 and the second bridge element 12.

It is remarked that due to the location of the strain element 19 on the midplane and the relative small and long first connection part 20 and second connection part 21, the strain element 20 will mainly elongate, but not bend, when the first distal extension part 7 tilts at the first bridge element 9 and the second distal extension part 10 tilts at the second bridge element 12. This further improves the measurement of the strain in the strain element 19 as a basis for determination of forces exerted by tissue or other material on the first jaw element 13 and the second jaw element 14.

A strain sensor, in particular a Fibre Bragg Grating (FBG) 22 provided in an optical fibre 23 is fixed in a hollow space in the strain element 19 (see FIG. 3) to measure the elongation of the strain element 19. The optical fibre 23 comprises a second FBG 24 that is not firmly fixed to the forceps frame 2. This second FBG 24 is provided to measure the effects of (change in) temperature.

Since the strain element 19 will only measure elongation caused by forces exerted on the first jaw element 13 and the second jaw element 14, there is no need for additional strain sensors to compensate other forces in the forceps frame 2, such as pulling and pushing forces used to operate the first jaw element 13 and the second jaw element 14. This results in a relatively simple measurement system comprising two Fibre Bragg Gratings provided in a single optical fibre 23.

It is remarked that forces exerted on the first jaw element 13 and the second jaw element 14 in opposite direction of the forces Ft1 and Ft2, for example by opening the first jaw element 13 and the second jaw element 14 in a tissue opening in which the jaw elements 13, 14 are placed, may result in a compression of the strain element 19 that can be measured by the FBG 22.

To prevent that the first extension 3 and the second extension 4 are bent beyond certain mechanical yield limits, the first extension 3 comprises a first bulge 25 and the second extension 4 comprises a second bulge 26. The first bulge 25 and the second bulge 26 have interlocking shapes to mechanically limit the extent of bending of the first extension 3 with respect to the second extension 4. In the unstressed position of the first jaw element 13 and the second jaw element 14, i.e. when no forces are exerted on the first jaw element 13 and the second jaw element 14, the distance between the first bulge 25 and the second bulge 26 substantially corresponds with the width of the slit 6. As a consequence, the first distal extension part 7 and the second distal extension part 10 can each bend until the first bulge 25 and the second bulge 26 have each moved over a distance of approximately half the width of the slit 6. This distance has been selected such that no plastic deformation in the first extension 3 and the second extension 4 will occur due to bending of the first distal extension part 7 and the second distal extension part 10.

It is thereby remarked that the first extension 3 and the second extension 4 are substantially symmetrical with respect to each other with respect to the midplane M. Only the first bulge 25 and the second bulge 26 are not symmetrical with respect to each other. This substantially symmetrical design has the advantage that when equal forces are exerted on the first jaw element 13 and the second jaw element 14, the first extension 3 and the second extension 4 will substantially equally bend.

The forceps construction 1 described above may be applied in any device or instrument in which an accurate feedback of the force that is exerted on the first jaw element 13 and the second jaw element 14 is desirable. The forceps construction 1 is in particular suitable for a surgical instrument for minimally invasive surgery, since accurate feedback of forces exerted on and by manipulated tissue is important to properly manipulate tissue.

FIG. 4 shows a surgical instrument 50 for minimally invasive surgery, comprising the forceps construction 1 as shown in FIG. 1.

The surgical instrument 50 comprises an elongate frame, formed by a handle part 51 and a shaft 52. The handle part 51 comprises an inner frame and a housing mounted on the inner frame. The shaft 52 is releasably mounted on the handle part 51, as will be described hereinafter. Further, the shaft 52 is rotatable about its longitudinal axis with respect to the handle part 51. This allows different rotational positions of the jaw elements 13, 14, with respect to the handle part 51 of the surgical instrument 50. A rotation knob 53 is provided to manually set a rotation position of the shaft 52 with respect to the handle part 51.

The rotation of the shaft about its longitudinal axis may for example be in the range of 300 degrees to 360 degrees, for example in the range of 160 degrees to 170 degrees in both rotation directions from a middle rotation position of the shaft. One or more stop elements may be provided to limit the range of rotation of the shaft 52.

A trigger device 54 is provided to operate the jaw elements 13, 14 of the forceps construction. The trigger device 54 is rotatably mounted in the handle part 51 of the surgical instrument 50.

The shaft 52 is hollow. Through the hollow shaft 52 an actuation rod 55 (see FIGS. 9-11) extends from the trigger device 53 to the actuation assembly of the forceps construction 1 to operate the forceps construction by manipulation of the trigger device 54.

The optical fibre 23 of the FBG's also runs through the hollow shaft 52. An actuator 56 (see FIGS. 7, 8) is provided in the handle part 51 to exert a feedback force on the trigger device 53 on the basis of a sensor signal based on the sensor signal obtained from the FBG.

A cable 57 is connected to the handle part 51. The cable 57 guides the optical fibre 23 from the handle part 15 to an interrogator device (not shown) arranged at a separate location. The interrogator device is configured to interrogate the one or more FBG's 22, 24 provided in the optical fibre and to provide a sensor signal representative for the force exerted on the jaw elements of the forceps construction 1.

The surgical instrument 50 comprises a controller, wherein the controller is arranged to control the actuator 56 on the basis of the sensor signal. The controller may be part of the handheld frame of the surgical instrument 50. In this embodiment, the sensor signal obtained by the interrogator device is guided through the cable 57 back to the handle part 51. In another embodiment, the controller may be provided as a separate device, or for example integrated with the interrogator device. In this embodiment the cable 57 is used to guide a control signal of the controller to the actuator 56. In yet an alternative embodiment, the controller and the interrogator device may be integrated in the handheld frame of the surgical instrument 50.

Since the optical fibre 23 runs through the handle part 51 and the shaft 52, the optical fibre 23 has to be able to follow rotation of the shaft 52 with respect to the handle part 51. The optical fibre 23 should not be damaged by the rotation of the shaft 52. Moreover, it should be avoided that the optical performance of the optical fibre decreases below a desired level due to a too small bending radius of the optical fibre 23.

Figures 5, 6:
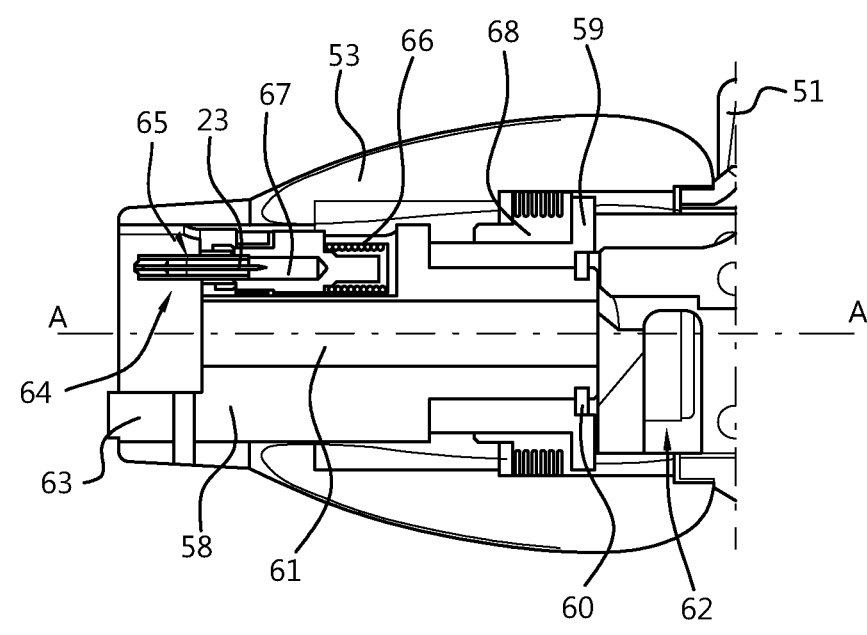
FIG. 5 shows a part of the surgical instrument at the connection of the shaft to the handle part of the surgical instrument.
FIG. 6 shows a fibre guide according to an aspect of the invention in more detail.

FIG. 5 shows the distal side of the handle part 51 for the releasable and rotatable connection of the shaft 52 in more detail. The handle part 51 supports a rotatable connection part 58 which is rotatable about the axis of rotation A-A which coincides with the longitudinal axis of the shaft 52 when mounted in the handle part 52. The rotatable connection part 58 is rotatably mounted on a fixed bearing 59 of the handle part 51. A lock plate 60 is provided to lock the rotatable connection part 58 on the fixed bearing 59.

The rotatable connection part 58 comprises a hollow channel 61 to receive the shaft 52 including the actuation rod 55 placed in the hollow shaft 52. The longitudinal axis of the actuation rod 55 when placed in the hollow shaft 52 will coincide with the axis of rotation A-A of the rotatable connection part 58 and the shaft 52.

The shaft 52 is releasably locked to the rotatable connection part 58 by a shaft locking mechanism 62 mounted on the frame of the handle part 51. The proximal end of the actuation rod 55 is releasably connected to the trigger device 54, for example comprising a ball catch mechanism. The rotation knob 53 is rotatably fixed to the rotatable connection part 58, such that rotation of the rotation knob 53 will result in rotation of the rotatable connection part 58 and therewith in rotation of the shaft 52, when connected to the rotatable connection part 58. The rotatable connection part 58 comprises an alignment element 63 to properly align the shaft 52 with the rotatable connection part 58 when the shaft 52 is mounted on the handle part 51. This alignment element 63 may also be used to transfer the rotational movement of the rotatable connection part 58 to the shaft 52.

As the shaft 52 is releasable from the handle part 51, the optical fibre 23 has to be provided in two parts that can be separated from each other. The shaft 52 comprises a first fibre part and a second fibre part of the optical fibre 23 is arranged in the handle part 51. A fibre connection device 64 is provided to optically connect the first fibre part and the second fibre part to each other when the shaft 52 is mounted on the handle part 51.

The fibre connection device 64 comprises a first connector arranged at the proximal end of the shaft 52 and a second connector 65 arranged at the distal end of the rotatable connection part 58. When the shaft 52 is mounted on the handle part 51, the first connector is pushed onto the second connector 65. To improve the connection between the first connector and the second connector 65, a spring element 66 is provided. The spring element 66 is biased in the distal direction to actively push a support element 67 supporting the second connector 65 on the first connector when the shaft 52 is mounted on the handle part 51.

The second connector 65 is arranged at a distance from the axis of rotation A-A of the rotatable connection part 58. As a result, rotation of the rotatable connection part 58 will lead to a difference in length of the path of the optical fibre 23 in the handle part 52. The optical fibre 23 therefore should allow a change in path length in the handle part 52. At the same time, it should be avoided that the bending radius of the optical fibre becomes too small as a small bending radius may have a negative effect on the optical performance of the optical fibre and/or may lead to damage of the optical fibre 23. For example, the bending radius of the optical fibre 23 suitable for use in the shown embodiment of the surgical instrument 50, should not be lower than a minimum fibre bending radius. Such minimum fibre bending radius may for example be 12 mm for a typical embodiment of an optical fibre having a diameter of 0.008 mm.

To facilitate rotation of the shaft 52 and the rotatable connection part 58 without increased risk on damage of the optical fibre 23 or substantial loss of optical performance of the optical fibre 23, a fibre guide 68 is provided.

FIG. 6 shows the fibre guide 68 in more detail. The fibre guide 68 comprises an outer cylindrical surface 69 having a helical groove 70 to guide the optical fibre 23 in a substantially helix shaped path. The outer cylindrical surface 69 of the fibre guide 68 is arranged concentrically with the axis of rotation A-A of the rotatable connection part 58 and therewith the shaft 52 when connected to the handle part 51.

The fibre guide 68 ensures that the change in path length of the optical fibre 23 can be accommodated by allowing the diameter of the loops of the optical fibre 23 in the helix shaped groove 70 to increase or decrease in dependence of the rotation of the rotatable connection part 58 with respect to the handle part 51. The diameter of the bottom surface of the groove 70, i.e. the smallest diameter of the groove 70 is larger than the minimum bending radius of the optical fibre 23 that can be allowed without having substantial performance loss. This ensures that the actual bending radius of the optical fibre will not come below this minimal bending radius.

The helical groove 70 defines a number of helical revolutions of 360 degrees around the longitudinal axis of the helical groove. The number of revolutions is in the shown embodiment between 6 and 8 revolutions. The number of revolutions may be adapted in dependence of the maximum rotation of the shaft 52 and the associated change in path length of the optical fibre 23 within the handle part 51.

The fibre guide 68 has an inner cylindrical surface 71 adapted to fit on the fixed bearing 59 of the handle part 51. The fibre guide 68 may be arranged to rotate together with the rotatable connection part 58 or may be fixed on the fixed bearing 59.

Figure 7:
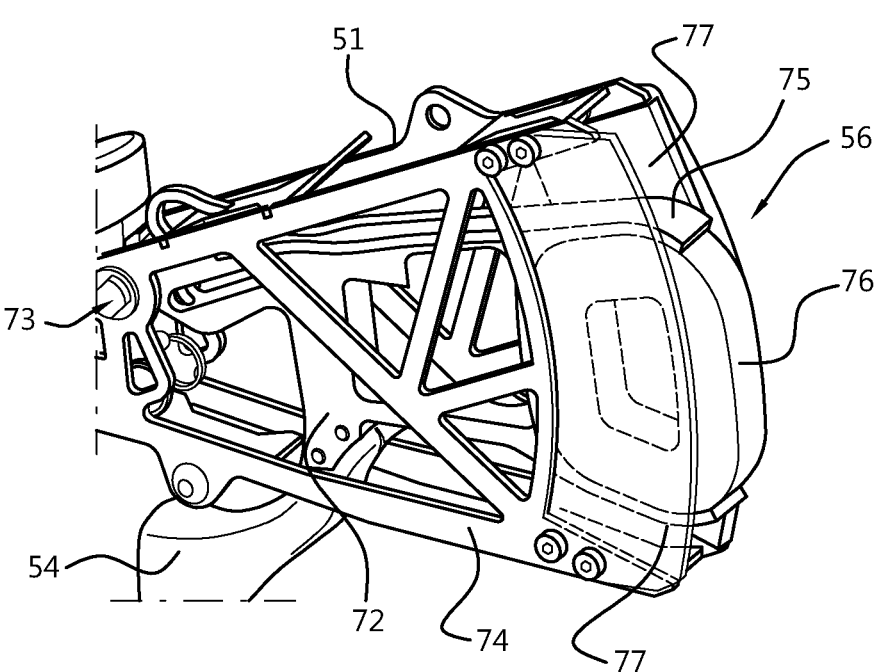
FIG. 7 shows an embodiment of a linear direct drive motor in the surgical instrument.

FIG. 7 shows the actuator 56 of the surgical instrument 50 in perspective view. The actuator 56 is a linear direct drive motor arranged in the handle part 51. The actuator 56 is provided to exert a feedback force on the trigger device 54. The trigger device 54 comprises a trigger 72 which is rotatably mounted at rotation axis 73 on the inner frame 74 of the handle part. The inner frame 74 is fixedly connected to the housing of the handle part 51 shown in FIG. 4.

The trigger 72 comprises an extension 75 on which a coil 76 is mounted. When the trigger is rotated about its rotation axis 73, the coil 76 will move along a path of movement. The actuator 56 comprises two permanent magnet assemblies 77, each aligned with the path of movement at opposite sides of the path of movement of the coil 76.

Figure 8:
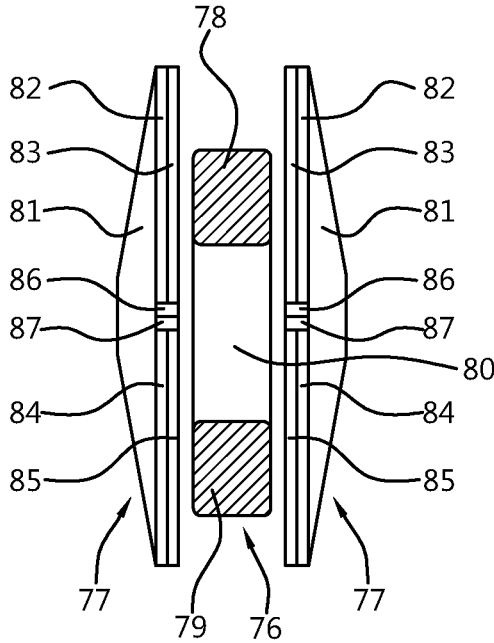
FIG. 8 shows the linear direct drive motor in more detail.

FIG. 8 shows the coil 76 and the permanent magnet assemblies 77 in more detail. The coil 76 comprises an upper coil part 78 and a lower coil part 79 connected to each other by side coil parts 80. The permanent magnet assemblies 77 each comprise a set of permanent magnets and a back iron 81. The set of permanent magnets comprises a first pair of magnets 82, 83 aligned with the upper coil part 78 and having an axial magnetization in a first direction and a second pair of magnets 84, 85 aligned with the lower coil part 79 and having an axial magnetization in a second direction opposite to the first direction.

Between the first set of magnets 82, 83 and the second set of magnets 84, 85, there is provided a third set of magnets 86, 87 having a tangential magnetization. It is remarked that the axial and radial direction of the magnetization are related to the rotational movement of the trigger 72 with respect to the rotation axis 73.

The arrangement of the permanent magnets is a Halbach array. The advantage of the use of a Halbach array of permanent magnets is that the magnetic field of the permanent magnets is augmented at one side of the permanent magnets, i.e. the side of the permanent magnets facing the coil 76, while at the opposite side of the permanent magnets the magnetic field will be close to zero.

The coil 76 and the permanent magnet assemblies 77 form a Lorentz motor. The axial magnetization of the first set of permanent magnets 82, 83 create a magnetic field in axial direction through the upper coil part 78, such that a current through the coil results in a Lorentz force in the tangential direction. Correspondingly, the axial magnetization of the second set of permanent magnets 84, 85 create a magnetic field in axial direction through the lower coil part 79, such that a current through the coil 76 also results in a Lorentz force in the tangential direction. Since the directions of axial magnetization of the first set of permanent magnets 82, 83 and the second set of permanent magnets 84, 85 are opposite to each other, and also the directions of the current through the upper coil part 78 and the lower coil part 79 are opposite to each other the resulting Lorentz forces in the upper coil part 78 and in the lower coil part 79 act in the same tangential direction.

The dimensions of the coil 76 and the permanent magnet assemblies 77 are designed such that at both ends of the range of movement of the trigger 73 the upper coil part 78 is still positioned between the first sets of permanent magnets 82, 83 and the lower coil part 79 is still positioned between the second sets of permanent magnets 84, 85.

An advantage of the Lorentz type direct drive motor as actuator 56 is that the actuation force of the motor is created directly between the trigger 73 and the handle part 51 of the surgical instrument. No separate moving parts are required and, furthermore, the coil 76 and the permanent magnet assemblies 77 are spaced with respect to each other. As a result, the linear direct drive motor can relatively easily be cleaned when needed and the actuator 56 will make little noise when actuated.

FIGS. 9, 10 and 11 show the distal end of the surgical instrument 50 comprising the forceps construction 1 arranged on the shaft 52. As described above, the shaft 52 is a hollow tube in which the actuation rod 55 is arranged. The shaft 52 and the actuation rod 55 are releasably mounted to the handle part 51 and the trigger device 54, respectively, as described with respect to FIG. 5. At the distal end of the actuation rod 55, an actuation rod locking mechanism 88 is provided to connect the actuation rod 55 to the actuation assembly of the forceps construction 1. The actuation rod locking mechanism 88 makes it possible to remove the actuation rod 55 out of the shaft 52 to facilitate proper cleaning and disinfection of both the shaft 52 and the actuation rod 55.

The actuation rod locking mechanism 88 comprises a spherical element 89 mounted at the distal end of the actuation rod 55, and a catch element 90 and a lock element 91 mounted at the proximal end of the actuation assembly. The lock element 91 comprises a recess in which the catch element 90 is placed. The catch element 90 comprises a catch space 92 to receive the spherical element 89. The catch element 90 is rotatable in the recess between a locking position, in which the spherical element 89 can be locked in the catch space 92 of the catch element 90, and a non-locking position, in which the spherical element 89 can move into and out of the catch space 92 of the catch element 90.

The catch element 90 comprises a groove 93 as a driving surface to receive a head of a screw driver. When the head of the screw driver is arranged in the groove 93 the catch element 90 can be rotated between the locking position and the non-locking position by rotation of the screw driver. Since the catch element 90 is arranged in the hollow shaft 52 an opening 94 is provided in the shaft 52 through which the screw driver can be arranged in the groove 93 of the catch element 94. In an alternative embodiment the driving surface, may be any surface, such as a slot, groove, or recess, suitable to receive a corresponding tool head for rotation of the catch element 90 between the locking position and the non-locking position.

The actuation rod 55 comprises a distal end surface 95 and the lock element 91 comprises a proximal end surface 96. When the spherical element 89 is arranged in the catch space 92, and the catch element 90 is rotated from the non-locking position to the locking position, the catch element 90 is arranged to pull the distal end surface 95 against the proximal end surface 96. This locking configuration in which the spherical element 89 is pulled by the catch element 90 in distal direction, while the proximal end surface 96 of the lock element 91 is pushed against the distal end surface 95 of the actuation rod 55 a tight connection between the lock element 91 and the actuation rod 55 can be obtained. The locking configuration can easily be released by rotation of the catch element 90 from the locking position to the unlocking position.

In the above embodiment, the surgical instrument may comprise the forceps construction 1. Aspects of the invention as described with respect to FIGS. 4-11 may also be applied in other embodiments of surgical instruments having at least one jaw element, but without the specific configuration of the forceps construction of FIGS. 1-3.

While specific embodiments have been described above, it will be appreciated that the invention may be practiced otherwise than as described. The descriptions above are intended to be illustrative, not limiting. Thus, it will be apparent to one skilled in the art that modifications may be made to the invention as described in the foregoing without departing from the scope of the claims set out below. It will further be appreciated that several mechanical layouts of the forceps are possible within the concept of the invention provided a slit or any other opening is arranged between the jaws of the forceps, said opening being arranged to guide the jaw reaction forces to separate parts of the frame of the surgical instrument.

The invention claimed is:

1. A forceps construction, comprising:
   a forceps frame having a distal end, the distal end comprising a first extension and a second extension, the first extension and the second extension extending in distal direction from a main part of the forceps frame,
   a first jaw element rotatably mounted on a first distal extension part of the first extension at a first axis of rotation,
   a second jaw element rotatably mounted on a second distal extension part of the second extension at a second axis of rotation, an actuation assembly connected to the first jaw element and the second jaw element to rotate the first jaw element and the second jaw element with respect to the forceps frame, wherein the first extension comprises the first distal extension part, a first proximal extension part and a first bridge element connecting the first distal extension part and the first proximal extension part, wherein the first bridge element is designed to facilitate bending of the first distal extension part with respect to the first proximal extension part when a force is exerted on the first jaw element, wherein the second distal extension comprises the second distal extension part, a second proximal extension part and a second bridge element between the second distal extension part and the second proximal extension part, wherein the second bridge element is designed to facilitate bending of the second distal extension part with respect to second proximal extension part when a force is exerted on the second jaw element, wherein a strain element is provided between the first extension and the second extension, wherein a proximal end of the strain element is connected to the main part of the forceps frame, and wherein a distal end of the strain element is connected to a proximal end of the first distal extension part and a proximal end of the second distal extension part, such that a force exerted on the first jaw element and/or the second jaw element results in bending of the first extension at the first bridge element and/or the second extension at the second bridge element, respectively, and consequently in elongation or compression of the strain element, wherein the strain element is mechanically substantially isolated from other forces in the forceps frame than forces resulting from bending of the first extension and/or the second extension, and wherein the forceps construction comprises a strain sensor mounted on or in the strain element to determine elongation or compression of the strain element.

2. The forceps construction of claim 1, wherein the strain element is an elongated element.

3. The forceps construction of claim 1, wherein a cross section of the strain element is smaller than a cross section of the first bridge element and a cross section of the second bridge element.

4. The forceps construction of claim 1, wherein the strain sensor is a Fibre Bragg Grating arranged in an optical fibre that is fixed on or in the strain element.

5. The forceps construction of claim 4, wherein the main part comprises in a proximal direction from the strain element a hollow channel in which the optical fibre is arranged.

6. The forceps construction of claim 4, wherein the optical fibre comprises a second strain sensor on or in the strain element to determine temperature effects.

7. The forceps construction of claim 1, wherein bending of the first extension with respect to the second extension is mechanically limited.

8. The forceps construction of claim 7, wherein the first extension comprises a first bulge and wherein the second extension comprises a second bulge, wherein the first bulge and the second bulge have interlocking shapes to mechanically limit the bending of the first extension with respect to the second extension.

9. The forceps construction of claim 1, wherein the first extension and the second extension are arranged at opposite sides of a midplane, wherein the first bridge element and the second bridge element are spaced from the midplane and the strain element is arranged on the midplane.

10. The forceps construction of claim 9, wherein the first extension and the second extension are substantially symmetrical with respect to the midplane.

11. A surgical instrument, in particular for minimally invasive surgery, comprising:

an elongate frame comprising at its distal end the forceps construction of claim 1, a trigger device to operate the first jaw element and the second jaw element, an actuation rod provided between the trigger device and the actuation assembly to transfer an actuation force from the trigger device to the first jaw element and the second jaw element, a strain sensor mounted on or in the strain element to provide a sensor signal, and an actuator to exert a feedback force on the trigger device on the basis of the sensor signal.

12. The surgical instrument of claim 11, wherein the strain sensor is a Fibre Bragg grating provided in an optical fibre.

13. The surgical instrument of claim 12, wherein the surgical instrument comprises a fibre Bragg grating interrogator device.

14. The surgical instrument of claim 11, wherein the surgical instrument comprises a controller wherein the controller is arranged to control the actuator on the basis of the sensor signal.

* * * * *